United States Patent [19]

Roy, III

[11] Patent Number: 4,868,107
[45] Date of Patent: Sep. 19, 1989

[54] METHOD FOR DETECTING ANTIBODIES AGAINST NEUROPEPTIDES AND DRUGS IN HUMAN BODY FLUID

[75] Inventor: Benjamin F. Roy, III, Silver Spring, Md.

[73] Assignee: The United States of America as represented by the Department of Health and Human Services, Washington, D.C.

[21] Appl. No.: 932,084

[22] Filed: Nov. 18, 1986

[51] Int. Cl.[4] .................. G01N 33/545; G01N 33/564
[52] U.S. Cl. ......................................... 435/7; 436/506; 436/531; 436/809; 436/811
[58] Field of Search .................... 435/7; 436/506, 531, 436/809, 811

[56] References Cited

PUBLICATIONS

*Biotechnology*, a catalogue of Fisher Scientific, 1983, p. 97.
Roy et al, *Proc. Natl. Acad. Sci. U.S.A.*, 83, 8739–8743, 1986.
Voller, *Diagnostic Horizon*, 2, No. 1, 1–2, 1978.
Fessel, (1962), *Arch Gen Psychiatry* 6:78–81, "Autoimmunity and Mental Illness".
Strahilevitz, et al, (1976), *Am. J. Psychiatry* 133:727–777, "Immunoglobulin Levels in Psychiatric Patients".
Amkraut, et al, (1973), *Arch Gen Psychiatry* 28:673–677, "Immunoglobulins and Improvement in Acute Schizophrenic Reactions".
Shopsin, et al, (1973), *Biological Psychiatry* 7:81–87, "Antinuclear Factor in Psychiatric Patients".
Baron et al, (1977), *Biological Psychiatry* 2:199–219, "Tissue-Binding Factor in Schizophrenic Sera: A Clinial and Genetic Study".
Garey, et al, (1974), *Biological Psychiatry* 8:75–88, "Focal Electroencephalographic Changes Induced by Anti-Septal Antobodies".
Boehme, et al, (1974), *Biological Psychiatry* 8:89–94, "Demonstration of Nuclear and Cytoplasmic Fluorescence in Brain Tissues of Schizophrenic and Nonschizophrenic Patients".
Mellsop, et al, (1973), *Arch Gen Psychiatry* 28:194–196, "Schizophrenia and Autoimmune Serological Reactions".

*Primary Examiner*—Robert J. Warden
*Assistant Examiner*—David A. Saunders
*Attorney, Agent, or Firm*—Fleit, Jacobson, Cohn, Price, Holman & Stern

[57] ABSTRACT

An immunochemical assay, particularly an enzyme-linked immunosorbent assay has been developed to detect in a sample of human body fluid the presence of antibodies against neuropeptides or drugs. The assay makes it possible to correlate and diagnose psychobiological disorders related to the alteration in the normal level of neuropeptides or their receptors.

2 Claims, No Drawings

METHOD FOR DETECTING ANTIBODIES AGAINST NEUROPEPTIDES AND DRUGS IN HUMAN BODY FLUID

BACKGROUND

1. Technical Field

The present invention is related generally to immunochemical assays. More particularly, the present invention is related to enzyme-linked immunoabsorbent assay (ELISA) for detecting in a sample of human body fluid the presence of particular antibodies having specific binding affinity for certain neuropeptides and drugs.

2. State of the Art

Despite the general principles for immunochemical assays being well known in the art, an assay having the reliability and specificity for detecting the presence of antibodies against neuropeptides or drugs in the human blood sample or body fluid has not heretofore been developed. Clearly, therefore, due to the lack of such an assay, the occurrence or presence in human body fluid of antibodies having specificity against certain neuropeptides or drugs has also not heretofore been established.

There are no prior descriptions of antibodies to brain peptides in human or an association of such antibodies with any disorder. However, the importance of idiotypic networks has been described in some autoimmune diseases. Antibodies raised against anti-hormone antibodies have the potential to bind and either block or stimulate the hormone receptor. Anti-idiotypes which mimic binding and physiological characteristics of hormone or neurotransmitter have been demonstrated for the B-adrenergic receptor in asthma and allergic rhinitis, insulin receptor in diabetes mellitus and the acetylcholine receptor in hyperthyroidism. In various systems or disease states the appearance of idiotypic and anti-idiotypic antibodies contributing to immune network regulation are cyclical and can potentially reverse or arrest the progression of pathology induced by the idiotype. It is possible that the dynamic steady state of an idiotype anti-idiotype network for brain peptides and their receptors is perturbed in the natural cyclical course of affective disorder and by the introduction of cross-reacting antigens in opiate substance abuse. Although one may postulate that the anti-idiotype is somehow pertinent to the pathophysiology of psychobiological disorders, this has not been conclusively demonstrated. However, it is possible that variations in the ratio of idiotype to anti-idiotype and variations in cerebral localization could contribute to variations in clinical presentation.

The present invention is the first to describe antibodies to brain peptides and has developed an immunodiagnostic test which provides more rational neuropathophysiological diagnostical and therapeutic interventions. Furthermore, the present invention is the first to demonstrate the potential influence of the immune network on CNS function. Data presented herein identifies and characterizes antibodies to B-endorphin, somatostatin, enkephalins and nerve growth factor, detected for the first time in human plasma, using an enzyme linked immunoabsorbent assay (ELISA). This demonstration provides a basis for identification and purification of antibodies to brain peptides from large samples of patients with neuropsychiatric impairment.

SUMMARY OF THE INVENTION

It is, therefore, an object of the present invention to provide a method for detecting in human body fluid the presence of antibodies having specific binding affinity for certain neuropeptides and/or drugs.

A further object of the present invention is to provide a method for correlating psychobiological disorders in humans with neuropeptide levels as reflected by blood level of antibodies having specificity for said neuropeptides.

Other objects and advantages will become evident as the detailed description of the present invention proceeds.

DETAILED DESCRIPTION OF INVENTION

The above and various other objects and advantages of the present invention are achieved by a method for detecting in a sample of human body fluid the presence of specific antibodies against brain peptides or drugs comprising the steps of:

(a) coating a microtiter plate with a solution of neuropeptide or drug to be detected, by incubating the plate for more than 24 hours with said solution at about 0° to 4° C. without a blocking step;

(b) then allowing a sample of immunoglobulin human body fluid in which the presence of antibody to the neuropeptide or drug is to be detected, to react with the coated plate in humidified air containing about 5-7% $CO_2$ for about 1.5 to 3 hours at about 37° C.;

(c) then washing the plate with a buffered detergent more than 5 times to remove unbound material from the plate;

(d) then allowing anti-human antibody conjugated with a marker entity to react for about 1.5 to 3 hours in humidified air containing about 5-7% $CO_2$ at about 37° C. with the washed plate of step (c) to allow binding of conjugated-antibody with the human antibody bound to the neuropeptide;

(e) then removing the unreacted material from the plate by washing more than 5 times as in step (c);

(f) then determining the presence of the marker by enzymatic, spectrophotometric, immunologic, fluorescentphotometric or radioisotopic assay and comparing with a control sample treated identically as in step (a) thru (e), a reading above the control being indicative of the presence of antibody against the neuropeptide or the drug.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereinunder are incorporated herein by reference.

The term "neuropeptides" or "brain peptides" includes such entities as B-endorphin, methionine-enkephalin, somatostatin, nerve growth factor (NGF), corticotropin, α-melanocyte stimulating hormone, substance P and the like.

MATERIALS AND METHODS

Enzyme Linked Immunoadsorbent Assay (ELISA).

Solutions of B-endorphin, somatostatin, nerve growth factor, corticotropin, alpha-melanocyte stimulating hormone or substance P are prepared at concentrations ranging from 1 µg/ml to 50 µg/ml in pH 9.4 coating buffer. The selection of concentration of the peptide to be assayed depends upon the character of the human sample to be assayed. Higher concentrations, e.g., about 20 µg/ml proved to be most suitable for serum, while a concentration of 10 µg/ml of peptide proved most suitable for assays of purified human IgG. However, a concentration of 10 µg/ml is most often used for assays. Other factors may necessitate modification of the ELISA. For example, the small molecular weight peptides (B-endorphin, methionine-enkephalin, 2.5S B-nerve growth factor) or dilute antigen preparations of about 1 µg/ml require longer periods to coat the plate, approximately 48 hours but greater than 24 hours. Larger molecular weight peptides, such as 7S B-nerve growth factor will coat the plate after a period ranging from a few hours to an overnight (about 16 hrs) incubation. Though some ELISA methods coat the plate for two hours, peptides such as B-endorphin are very sticky and will coat any plastic within minutes; since most control peptides do not similarly adhere to plastic overnight, incubations from about 24 to 48 hours allow for more equitable comparison. After centrifugation at about 3,000 rpm for up to 30 minutes, peptide solutions are pipetted in a 100 µl volume into a microtiter plate such as an Immulon I polystyrene plate (Dynatech Labs Inc.) and allowed to stand at 0° to 4° C. for 24 to 48 hours. The plate is washed with buffered detergent such as 0.5% Tween-20 (Fisher Scientific Co.) in phosphate buffered saline (PBS, pH 7.3 without calcium or magnesium). Though some ELISA methods have a blocking step in which the plate is incubated with 100 µl of 0.5% bovine plasma albumin in distilled water for 20 minutes at room temperature to reduce nonspecific binding, this can interfere in the assay against a small molecular weight peptide. Therefore, the blocking step is omitted and human body fluid or immunoglobulin samples can be used straight or prepared with a small percentage (0.5-1.0%) of normal goat serum (other animal serums may also suffice, e.g., fetal calf serum or normal sheep serum). The human samples to be assayed are spun at about 3,000 rpm for up to 30 minutes prior to the assay. Then 100 µl of human body fluid or immunoglobulin is added, the plate is covered and incubated at about 37° C. for approximately 1.5 to 3 hours in a forced draft 5-7% $CO_2$ countertop incubator (Forma Scientific). The plate is then washed a minimum of 5 times and 100 µl of a 1:200 dilution of an alkaline phosphate conjugated goat anti-human immunoglobulin (heavy chain specific) antibody (Sigma Chemical Co., St. Louis, Mo.) is pipetted into each well. After 2 hours incubation at about 37° C. the plate is washed a minimum of 5 times and 100 µl of the AP substrate p-nitrophenyl phosphate (disodium salt) dissolved in 10% diethanolamine is added to each well. The plate is wrapped, for example, in aluminum foil to protect from the light, and the reaction is allowed to proceed at about 37° C. in the dark. Substrate catalysis reflects the degree of goat antibody bound to human immunoglobulin which in turn is bound to neuropeptide and is determined by optical industry units read at 405 nm on an automatic microELISA spectrophotometer (Dynatech Instruments, Inc., Torrence, Calif.). Values represent the means ±S.D. of triplicate optical density readings ranging from 30 minutes to 2 hours reaction time. The reaction time varies with the concentration of the peptide bound to the plate and the nature and concentration of the sample being assayed. Table 1 shows the results obtained using the ELISA of the present invention.

It is noted that although an immuno-enzymatic-spectrophotometric method for detecting the marker (alkaline phosphatase) is illustrated here, other methods such as fluorescent-photometric, radioisotopic and the like or a combination of such methods well known in the art can be used to detect the marker or the ligand. A control sample is preferably included for comparison.

TABLE 1

| Human Anti-β-Endorphin Immunoglobulin G | | | |
|---|---|---|---|
| Subject | Age | Sex | Activity for β-Endorphin |
| Major Depression | | | |
| 1. | 44 | F | 0.641 |
| 2. | 44 | F | 0.791 |
| 3. | 34 | F | 0.887 |
| 4. | 35 | F | 0.239 |
| 5. | 54 | F | 0.061 |
| 6. | 60 | F | 0.200 |
| 7. | 54 | F | 0.083 |
| 8. | 56 | M | 0.168 |
| 9. | 40 | M | 0.020 |
| Controls: | | | |
| 10. | 52 | F | 0.034 |
| 11. | 23 | F | 0.041 |
| 12. | 52 | F | 0.365 |
| 13. | 26 | F | 0.060 |
| 14. | 29 | F | 0.048 |
| 15. | 52 | F | 0.279 |
| 16. | 44 | F | 0.112 |
| 17. | 44 | F | 0.049 |
| 18. | 23 | F | 0.143 |
| 19. | 21 | F | 0.070 |
| 20. | 34 | F | 0.069 |

Reactivity for B-endorphin remained present after pepsin digestion of IgG to F(ab')$_2$ fragments indicating that the ELISA reflected actual interaction of an antigen recognition site on the antibody with the neuropeptide bound to the ELISA plate. Purified IgG from subject 3 was combined with pepsin in a ratio of 100:2 and incubated overnight at 37° C. at pH 4.5 in acetate buffer. The pH was then raised to 8.0 by the addition of 1 M NaOH, and the digest applied to a Sephadex G-200 column and F(ab')$_2$ fragments collected and evaluated by Ouchterlony technique. The fraction with reactivity to sheep anti-human F(ab')$_2$ but not goat anti-human (Fc)IgG was evaluated for activity against B-endorphin and ACTH. The ELISA was performed as described above utilizing F(ab) or purified IgG as the primary antisera at concentrations of 20 µg/100 µl. Second antibodies to detect binding of F(ab')$_2$ were: AP-conjugated goat anti-human kappa chain and anti-human lambda chain (Sigma Chemical Co.), each at a 1:200 dilution, or a combination of the two, each at 1:400 dilutions. Values represent optical density readings, $OD_{405}$ at 15 minutes. The results are shown in Table 2.

TABLE 2

| Recognition of β-Endorphin by F(ab)'2 | | |
|---|---|---|
| Subject No. 3 | β-Endorphin | ACTH |
| F(ab)'2 fragments | | |
| α-kappa chain | .542 ± .017 | .075 ± .036 |
| α-lambda chain | .442 ± .127 | .035 ± .003 |
| α-kappa + α-lambda | .528 ± .117 | .099 ± .086 |
| IgG: | | |
| α-kappa chain | 1.287 ± .275 | .218 ± .052 |
| α-lambda chain | 1.258 ± .073 | .209 ± .041 |

TABLE 2-continued

| Recognition of β-Endorphin by F(ab)'2 | | |
|---|---|---|
| Subject No. 3 | β-Endorphin | ACTH |
| α-kappa + α-lambda | 1.136 ± .107 | .291 ± .065 |

Affinity Chromatography

Affinity chromatography was used for isolating specific anti-B-endorphin IgG from rabbit and human Ig samples. Twenty ml of sepharose 4B (Pharmacia) was washed with 4 liters of distilled $H_2O$ followed by a wash with 500 ml of 0.1 M $NaHCO_3$, about pH 8.3 containing 0.5 M NaCl. The supernatant was aspirated and the slurry transferred to a beaker. At this point B-endorphin (or somatostatin, nerve growth factor and the like was added in a concentration of at least 0.5 mg of peptide per ml of sepharose (antibody can be recovered with as little as 0.1 mg of peptide per ml of sepharose but higher concentrations are preferred). The peptide was allowed to couple to the sepharose 4B with gentle stirring at room temperature for 2 hours and then overnight at about 4° C. The slurry was then allowed to settle. The supernatant was aspirated and centrifuged at approximately 3,000 rpm. The volume and optical density were measured and the percentage of peptide bound determined. Any remaining peptide and coupling buffer were removed from the slurry by washing with 3 liters of 0.2 M borate buffered saline, about pH 8.1 until the optical density of 280 nm was zero. The slurry was washed with 0.1 M Tris-HCl buffer, approximately pH 8 overnight at about 4° C. to block remaining active unbound sites. The product was then washed with 0.1 M glycine HCl, approximately pH 2.8 followed by a wash with 0.2 M borate buffered saline, pH 8.1 with 0.04% sodium azide until the pH of the effluent equalled that of the borate buffered saline. Normal rabbit IgG and rabbit anti-B-endorphin IgG (Immuno Nuclear Corp, Stillwater, Minn.) were eluted from Protein A columns and dialyzed against PBS at 4° C. Samples were adsorbed on an affinity column containing synthetic human B-endorphin coupled to cyanogen bromide activated sepharose 4B (0.46 mg B-endorphin/ml of sepharose). The column was washed with PBS until absorbance at 280 nm was zero. Elution was performed using 3M potassium thiocyanate and 4M guanidine hydrochloride. Rabbit effluents and eluates were dialyzed and concentrated by vacuum dialysis to equivalent protein concentrations as determined by optical density units on a spectrophotometer. Human effluents and eluates were concentrated by ultrafiltration on XM100 Diaflo membranes (Amicon Corp. 6 Lexington, MA) and tested by ELISA for activity to B-endorphin. Reactivity for B-endorphin could be separated in column eluates and was not present in column effluents (Tables 3 and 4) at equivalent IgG concentrations.

Immunoprecipitation.

Affinity chromatography purified anti-B-endorphin IgG was incubated with B-endorphin [$^{125}$I](New England Nuclear Research Products, Boston, Mass.) overnight at 4° C. and then precipitated with an equivalent amount of sheep anti-human IgG antibody; equivalence determined in pilot immunoprecipitation assays. Tables 3 and 4 show the results obtained by affinity column purification.

TABLE 3

| Affinity Column Purification of Rabbit Anti-β-Endorphin Immunoglobulin G | | | | |
|---|---|---|---|---|
| | β-Endorphin | α-MSH | ACTH | SP |
| Serum | | | | |
| Normal rabbit0 | 0 | 0 | 0 | 0 |
| α β-Endorphin | 0.279 ± .004 | 0.081 ± .017 | 0.084 ± .016 | 0.040 |
| IgG | | | | |
| Normal rabbit | 0 | 0 | 0 | 0 |
| α β-Endorphin | 0.513 ± .026 | 0.185 ± .022 | 0.141 ± 0 | 0.036 |
| β-Endorphin Column Eluates: | | | | |
| Normal rabbit IgG | 0 | 0 | 0 | 0 |
| α β-Endorphin IgG | 0.850 ± .081 | 0.179 ± .035 | 0.081 ± .006 | 0.109 |
| Effluents: | | | | |
| Normal rabbit IgG | 0 | 0 | 0 | 0 |
| α β-Endorphin IgG | 0.032 ± .001 | 0.036 ± .001 | 0.035 ± 0 | 0.033 |
| IgG depleted antiserum | 0.031 ± .001 | 0.030 ± .001 | 0.040 ± .003 | 0.032 |

Values represent the mean ±S.D. of triplicate $OD_{405}$ taken at 60 minutes.

TABLE 4

| Affinity Column Purification of Human Anti-β-Endorphin IgG | | | | |
|---|---|---|---|---|
| Subject | IgG | β-Endorphin | α-MSH | ACTH |
| 1. IgG depleted serum | <5 | .038 ± .008 | .022 ± .001 | .029 ± .003 |
| serum 1:100 | 16,200 | .414 ± .096 | .176 ± .023 | .233 ± .024 |
| 1:500 | 3,240 | .169 ± .004 | .069 ± .015 | .124 ± .026 |
| 1:1000 | 1,620 | .117 ± .020 | .070 ± .017 | .071 ± .009 |
| IgG | 300 | .231 ± .013 | .180 ± .027 | .066 ± .053 |
| eluate: | | | | |
| fraction 1 (KSCN) | 300 | 1.120 ± .136 | .111 ± .012 | .097 ± .013 |
| fraction 2 (KSCN) | 300 | .691 ± .104 | .072 ± .019 | .038 ± .004 |
| fraction 3 (GHCl) | 170 | .591 ± .025 | .048 ± .001 | .044 ± .004 |
| effluent | 300 | .094 ± .011 | .046 ± .004 | .083 ± .038 |
| 2. IgG depleted serum | <5 | .045 ± .003 | .032 ± .002 | .040 ± 0 |
| serum 1:100 | 10,000 | .401 ± .044 | .277 ± .028 | .102 ± .081 |
| 1:500 | 2,020 | .162 ± .004 | .069 ± .007 | .132 ± .027 |
| 1:1000 | 1,010 | .117 ± .004 | .051 ± .002 | .067 ± .012 |
| IgG | 600 | .565 ± .100 | .119 ± .030 | .077 ± .001 |

TABLE 4-continued

| Affinity Column Purification of Human Anti-β-Endorphin IgG | | | | |
|---|---|---|---|---|
| Subject | IgG | β-Endorphin | α-MSH | ACTH |
| eluate: | | | | |
| fraction 1 (KSCN) | 600 | .666 ± .031 | .056 ± .006 | .044 ± .002 |
| fraction 2 (GHCl) | 200 | .241 ± .018 | .038 ± .001 | .037 ± .001 |
| effluent | 600 | .124 ± .103 | .038 ± .001 | .038 ± .009 |
| 3. IgG depleted serum | <5 | .035 ± .003 | .034 ± .004 | .035 ± .001 |
| serum 1:100 | 11,300 | .498 ± .021 | .233 ± .007 | .252 ± .011 |
| 1:500 | 2,260 | .376 ± .008 | .161 ± .072 | .169 ± .064 |
| 1:1000 | 1,130 | .261 ± .084 | .080 ± .004 | .092 ± .016 |
| IgG | 450 | .422 ± .110 | .094 ± .011 | .050 ± .0 |
| eluate: | | | | |
| fraction 1 (KSCN) | 600 | .813 ± .029 | .197 ± .014 | .119 ± .013 |
| fraction 2 (KSCN) | 450 | .827 ± .021 | .168 ± .003 | .094 ± .011 |
| fraction 3 (GHCl) | 300 | .307 ± .004 | .048 ± .008 | .037 ± .001 |
| effluent | 450 | .080 ± .001 | .033 ± .002 | .028 ± .001 |

Anti-B-endorphin IgG 0.1 mg immunoprecipitated 15% of [$^{125}$I]-B-endorphin activity. It inhibited binding of rabbit antisera to [$^{125}$I]-B-endorphin in a competitive radioimmunoassay from New England Nuclear (Control=4,783 anti-B-endorphin IgG=986 for a 79% reduction). The antibody has neuropharmacological activity. In opiate receptor assays the idiotypic anti-B-endorphin IgG consistently inhibits the binding of [$^{125}$I]-B-endorphin to its natural receptor on homogenized rat brain membranes (Table 5).

TABLE 5

| Anti-β-Endorphin IgG Inhibits Binding To The Opiate Receptor | | | |
|---|---|---|---|
| Sample | [IgG] | Specific Binding | % Inhibition |
| Control | | 6,558 | |
| Anti-β-endorphin IgG | 78 μg | 2,634 | 60 |
| Normal IgG | 78 μg | | +6 |

The specificity for β-endorphin is supported by the inability of the antibody to immunoprecipitate [$^{125}$-I]-morphine (Roche Diagnostics Inc.), as well as, its inability to inhibit the activity of an unrelated anti-measles IgG (Table 6).

TABLE 6

| Effect of Anti-β-Endorphin Antibody on Anti-Measles Antibody Activity | | |
|---|---|---|
| | Control | Anti-β-Endorphin IgG |
| Media | — | 0.069 |
| Measles antiserum titer: | | |
| 1:200 | 0.658 | 0.583 |
| 1:400 | 0.562 | 0.461 |
| 1:800 | 0.410 | 0.381 |
| 1:1600 | 0.246 | 0.321 |
| 1:3200 | 0.168 | 0.254 |
| 1:6400 | 0.137 | 0.194 |

Vero cell (African Green monkey kidney cells, American Type Culture Collection, Rockville, MD) monolayers were infected with Edmonston strain measles virus as previously described. Lysates of the infected Vero cells were adsorbed to Immulon I ELISA (Dynatech) plates overnight at 4° C. Values represent the average of duplicate OD$_{405}$ at 20 minutes reaction time.
Additional reactivities have been detected against related opiate peptides. Table 7 compares a positive for antibody for β-endorphin with a nonreactive subject.

TABLE 7

| Antibody Reactive with Enkephalin Peptides | | | | |
|---|---|---|---|---|
| | Methionine Enkephalin | β-Lipotropin 88–91 | Leucine Enkephalin | Pro-enkephalin |
| Positive | 0.537 | 0.373 | 0.293 | 0.320 |
| Negative | 0.167 | 0.144 | 0.088 | 0.094 |

The data presented herein clearly demonstrate that the ELISA of the present invention detects antibodies to human brain peptides. Moreover, serum or IgG reactivity in the ELISA with B-endorphin reliably reflects the presence of an antibody with neuropharmacological specificity for B-endorphin. Reactive antibody is isolated from serum in purified IgG and is not present in IgG depleted serum. Reactivity can be further isolated from purified IgG by affinity chromatography immunoabsorption to cyanogen bromide activated sepharose 4B with covalently coupled B-endorphin. Reactive antibody demonstrates specificity and immunoprecipitates radiolabelled B-endorphin but does not immunoprecipitate related opiate compounds. The antibody does not interfere with the activity of an unrelated antiserum but does not inhibit the activity of a related rabbit anti-B-endorphin antiserum.

Similarly, immunoglobulin G in human plasma with reactivity to somatostatin from 5/10 patients with affective disorder and 1/8 controls through the use of the ELISA of the present invention has been demonstrated (Table 8). This is the first demonstration of an antibody n human plasma or serum with specificity for somatostatin, a neuropeptide that participates in synaptic modulation. Activity for somatostatin was detected in serum (Table 8) and was present in the IgG fraction (Table 9). The antibody immunoprecipitates somatostatin-14[$^{125}$I-]and its activity is retained in F(ab')$_2$ fragments (Table 10). Specific antibody was recovered by affinity chromatography when IgG was immunoabsorbed to somatostatin coupled to cyanogen bromide activated sepharose 4B (Table 11).

TABLE 8

| Anti-Somatostatin Activity in Human Serum[a] | | | |
|---|---|---|---|
| | | OD$_{405}$ | |
| Subject | Somatostatin | ACTH | Anti-Somatostatin Activity |
| Major Depression: | | | |
| 1. | 0.685 ± 0.112 | 0.083 ± 0.003 | 0.602 |
| 2. | 0.424 ± 0.002 | 0.076 ± 0.003 | 0.348 |
| 3. | 0.312 ± 0.047 | 0.089 ± 0.016 | 0.223 |
| 4. | 0.266 ± 0.015 | 0.080 ± 0.011 | 0.186 |
| Normal Volunteers: | | | |
| 5. | 0.124 ± 0.009 | 0.061 ± 0.004 | 0.063 |
| 6. | 0.101 ± 0.018 | 0.058 ± 0.009 | 0.043 |
| 7. | 0.155 ± 0.021 | 0.081 ± 0 | 0.074 |
| 8. | 0.168 ± 0.005 | 0.079 ± 0.006 | 0.089 |
| 9. | 0.135 ± 0.016 | 0.059 ± 0.005 | 0.076 |
| 10. | 0.143 ± 0.004 | 0.064 ± 0.001 | 0.079 |

[a]Values represent the mean ± SD of triplicate OD$_{405}$ at 2 hours determination. The concentration of IgG was equilibrated to 174 μg/100 μl by quantitative radial immunodiffusion (Meloy Laboratories, Springfield, VA). The concentration of antigen was 1 μg/100 μl. Anti-somatostatin activity was determined by subtracting the reactivity with ACTH from the reactivity with somatostatin.

TABLE 9
Human Immunoglobulin G with Reactivity To Somatostatin

| Subject | Age | Sex | Somatostatin | ACTH | Anti-Somatostatin |
|---|---|---|---|---|---|
| Major Depression: | | | | | |
| 1. | 38 | M | 0.674 ± 0.065 | 0.070 ± 0.001 | 0.604 |
| 2. | 44 | F | 0.110 ± 0 | 0.047 ± 0.003 | 0.063 |
| 3. | 35 | F | 0.716 ± 0.063 | 0.149 ± 0.025 | 0.567 |
| 4. | 44 | F | 0.060 ± 0.011 | 0.043 ± 0.003 | 0.017 |
| 5. | 34 | F | 0.183 ± 0.057 | 0.051 ± 0.003 | 0.132 |
| 6. | 54 | F | 0.090 ± 0.002 | 0.060 ± 0.006 | 0.030 |
| 7. | 60 | F | 0.645 ± 0.035 | 0.058 ± 0.004 | 0.587 |
| 8. | 54 | F | 0.410 ± 0.020 | 0.063 ± 0.002 | 0.347 |
| 9. | 56 | M | 0.358 ± 0.024 | 0.045 ± 0.031 | 0.313 |
| 10. | 46 | M | 0.211 ± 0.012 | 0.062 ± 0 | 0.149 |
| Normal Volunteers: | | | | | |
| 11. | 44 | F | 0.287 ± 0.034 | 0.044 ± 0.002 | 0.243 |
| 12. | 33 | F | 0.077 ± 0.011 | 0.050 ± 0.001 | 0.027 |
| 13. | 33 | F | 0.070 ± 0.003 | 0.052 ± 0 | 0.018 |
| 14. | 28 | F | 0.076 ± 0.002 | 0.060 ± 0 | 0.016 |
| 15. | 30 | F | 0.181 ± 0.014 | 0.056 ± 0.003 | 0.125 |
| 16. | 28 | F | 0.066 ± 0.043 | 0.043 ± 0.001 | 0.023 |
| 17. | 23 | F | 0.070 ± 0.001 | 0.065 ± 0.010 | 0.005 |
| 18. | 40 | F | 0.055 ± 0.001 | 0.046 ± 0.002 | 0.009 |

The ELISA was performed as described in Materials and Methods section. Values represent the mean ± S.D. of triplicate $OD_{405}$, at 30 minutes reaction time. Anti-somatostatin activity was derived by subtracing the reactivity with ACTH from the reactivity with somatostatin. The IgG concentrations were equilibrated to 200 ng/100 μl. Somatostatin and ACTH were attached to the plate overnight at 4° C.

TABLE 10
Recognition of Somatostatin by F(ab')₂ Fragments

| Subject | $OD_{405}$ Somatostatin | ACTH | Anti-Somatostatin Activity |
|---|---|---|---|
| 1. F(ab')₂ fragments | | | |
| α-kappa chain | 0.328 ± 0.023 | 0.043 ± 0.001 | 0.285 |
| α-lambda chain | 0.311 ± 0.002 | 0.037 ± 0.003 | 0.274 |
| α-kappa + α-lambda | 0.366 ± 0.009 | 0.058 ± 0.006 | 0.308 |
| 8. F(ab')₂ fragments | | | |
| α-kappa chain | 0.165 ± 0.006 | 0.100 ± 0.003 | 0.065 |
| α-lambda chain | 0.087 ± 0.010 | 0.036 ± 0.004 | 0.049 |
| α-kappa + α-lambda | 0.158 ± 0.015 | 0.043 ± 0.002 | 0.115 |

The ELISA was performed as described in Materials and Methods section utilizing F(ab')₂ or purified IgG as the primary antisera (10 μg/100μl). Second antibodies to detect binding of F(ab')₂ were: alkaline phosphatase conjugated goat anti-human kappa chain, goat anti-human lambda chain (Sigma Chemical Co., St. Louis, MO) each at a 1:200 dilution, or a combination of the two, each at 1:400 dilutions. Values represent the mean ± SD of triplicate $OD_{405}$ at 60 minutes.

TABLE 11
Affinity Column Purification of Human Anti-Somatostatin IgG

| Subject | IgG | $OD_{405}$ Somatostatin | α-MSH | ACTH |
|---|---|---|---|---|
| 1. IgG depleted serum | <5 | 0.033 ± 0 | ND | 0.033 ± 0.002 |
| IgG | 2,000 | 0.985 ± 0.029 | ND | 0.037 ± 0.002 |
| eluate | 2,000 | 1.326 ± 0.048 | ND | 0.020 ± 0.010 |
| effluent | 2,000 | 0.018 ± 0.006 | ND | 0.005 ± 0.001 |
| 2. IgG depleted serum | <5 | 0.032 ± 0.003 | 0.028 ± 0.003 | 0.026 ± 0.001 |
| IgG | 1,091 | 1.075 ± 0.087 | 0.029 ± 0.001 | 0.029 ± 0.002 |
| eluate | 760 | 1.171 ± 0.069 | 0.094 ± 0.006 | 0.078 ± 0.008 |
| effluent | 760 | 0.230 ± 0.011 | 0.037 ± 0.004 | 0.035 ± 0.003 |
| 4. IgG depleted serum | <5 | 0.048 ± 0.001 | 0.036 ± 0.003 | 0.037 ± 0.004 |
| IgG | 1,070 | 1.059 ± 0.189 | 0.066 ± 0.003 | 0.055 ± 0.001 |
| eluate | 621 | 1.208 ± 0.125 | 0.082 ± 0.011 | 0.065 ± 0.005 |
| effluent | 811 | 0.067 ± 0.001 | 0.051 ± 0.004 | 0.045 ± 0.003 |

The search for antibodies to B-endorphin was prompted by the clinical manifestations of psychotically depressed patients with concomitant somatic and orofacial sensory complaints that were limited to the innervation of the branchial arches, i.e., cranial nerves VI, VII, IX and X. The restricted range of central involvement implied potential selective dysfunction of specific neurotransmitter pathways, in particular, opiate pathways subserving analgesia. A centrally placed lesion that impaired analgesia might account for the perceived sensory disturbance in the absence of demonstrable peripheral pathology. Therefore, work was undertaken to demonstrate the possible existence of antibodies to B-endorphin by devising and using an ELISA system. Human autoantibody to the brain peptide B-endorphin was thus identified in patients with depression using the newly developed enzyme linked immunoabsorbent assay (ELISA) and isolated by affinity chromatography described herein supra.

The sensitivity and specificity of this assay was tested using rabbit anti-B-endorphin antiserum (Immuno Nuclear Corp., Stillwater, Minn.). Initially, rabbit and human samples were assayed against rat B-endorphin (Sigma Chemical Co., St. Louis, Mo,) but when human synthetic B-endorphin became available, all tests employed the human peptide. Additionally, the initial method employed an indirect sandwich ELISA that was satisfactory for experimentally induced rabbit antisera but which demonstrated considerable difficulties in interpretation due to nonspecific binding and wide intra-test and inter-test variability with human IgG. The direct ELISA became the preferred test providing more reliability. The rabbit anti-B-endorphin antiserum was demonstrated to have relatively high specificity for B-endorphin with negligible reactivity to bovine plasma albumin (<3.5%) or other human neuropeptides (2.5–7.9%). In similar experiments comparable specificity was found using antisera to other neuropeptides including adrenocorticotrophic hormone (ACTH), alpha-melanocyte stimulating hormone (a-MSH), and substance P (SP), firmly establishing that each of these neuropeptides bound to ELISA plates. Table 12 shows the results obtained with rabbit antisera.

TABLE 12
Specificity of Rabbit Antisera for Human Neuropeptides

| | Rabbit Antisera | | | | | |
|---|---|---|---|---|---|---|
| | β-Endorphin | Bovine albumin | ACTH | α-MSH | Somatostatin | SP |
| β-Endorphin | 1.341 | 0.079 | 0.052 | 0.053 | 0 | 0.013 |

TABLE 12-continued

Specificity of Rabbit Antisera for Human Neuropeptides

| | Rabbit Antisera | | | | | |
|---|---|---|---|---|---|---|
| | β-Endorphin | Bovine albumin | ACTH | α-MSH | Somatostatin | SP |
| Bovine plasma albumin | 0.046 | 1.185 | 0.259 | 0.002 | 0.046 | 0.071 |
| ACTH | 0.047 | 0.113 | 1.299 | 0.157 | 0 | 0 |
| α-MSH | 0.034 | 0.021 | 0.019 | 0.874 | 0 | 0 |
| Somatostatin | 0.106 | 0.025 | 0.123 | 0.019 | 1.193 | 0.066 |
| Substance P | 0.049 | 0.027 | 0.043 | 0 | 0 | 0.805 |

TABLE 13

Rabbit Anti-β-Endorphin Antiserum Binding to β-Endorphin

| β-Endorphin | $OD_{405}$ | |
|---|---|---|
| μg/100 μl | Rabbit anti-β-endorphin antiserum | |
| | 1:100 | 1:1000 |
| 10.0 | 1.012 | 0.158 |
| 1.0 | 0.942 | 0.128 |
| 0.1 | 1.270 | 0.542 |
| 0.01 | 0.533 | 0.265 |
| 0.001 | 0.226 | 0.069 |
| 0.0001 | 0.215 | 0.028 |

Earlier experiments were performed at room temperature and required reading times of 60 minutes or more to reach maximal readings above $1.0_{405}$. Therefore, experiments with varying conditions were performed to improve the detection of antibody. It was reasoned that incubation at physiological temperatures might approximate body temperature and improve binding of the antibody to B-endorphin, as well as, the binding of goat antibody to human or rabbit IgG. As shown in Table 14 there was considerable variation in the results that depended upon the conditions of the ELISA.

TABLE 14

Variations in ELISA Results Linked to ELISA Conditions

| Antigen Incubation | Sample incubation | Anti-Rabbit IgG | Substrate | $OD_{405}$ |
|---|---|---|---|---|
| 1. 0° C. | 37° C. | 37° C. | 37° C. | 0.875 |
| 2. room temperature | 37° C. | 37° C. | 37° C. | 0.315 |
| 3. 0° C. | room temp | room temp | 37° C. | 0.185 |
| 4. 0° C. | room temp | room temp | room temp | 0.120 |

The time allowed to coat the plate varied from an overnight to a 48 hour incubation. Unlike rabbit antiserum which had optimal binding at concentrations of 0.1 μg/100 μl of B-endorphin that had incubated overnight, human serum and IgG demonstrated optimal binding to B-endorphin concentrations of 1 μg/100 μl that had incubated for 48 hours (TABLE 15).

TABLE 15

24 hour vs. 48 hour Coating Period
Effect on Anti-β-Endorphin Activity

| | $OD_{405}$ | |
|---|---|---|
| | 24 HOURS | 48 HOURS |
| 1. | 0.436 | 0.641 |
| 2. | 0.297 | 0.791 |
| 3. | 0.328 | 0.887 |

Purified IgG was also examined after either ammonium sulfate precipitation or Protein A (*Staphylococcus aureus*) column separation. Serum samples were obtained from a general pool of six blood donors, nine healthy normal volunteers, and 12 psychiatric patients meeting DSM III criteria for either major depression (N=9) or personality disorder (N=3) who were sequentially admitted over a several month period to an NIMH Clinical Center psychiatric unit. The results with both procedures were similar.

Nerve growth factor was initially believed to function as a trophic factor for the peripheral nervous system exclusively. However, a growing number of studies indicate an important role for NGF in sustaining cholinergic and catecholaminergic neurons of the central nervous system. Nerve growth factor mRNA is most concentrated within the CNS in the hippocampus and cortex and synthesized in the areas. It is retrogradely transported from the hippocampus to cholinergic neurons of the medial septal nucleus and the nucleus of the diagonal band of Broca and from frontal and occipital cortex to the cholinergic nucleus basalis of Meynert. Nerve growth factor binds the NGF receptor at these sites and increases the activity of choline acetyltransferase. Antiserum to NGF blocks the anticipated increase in choline acetyltransferase activity in cultures of straital neurons.

Alzheimer's disease is associated with neuropathological degeneration of hippocampal and cortical neurons and cholinergic neurons of the basal nucleus of Meynert. There is an accompanying reduction in choline acetyltransferase and acetylcholinesterase levels. Cholinomimetic drugs enhance memory while anticholinergic drugs impair memory. As a result, the destruction of cholinergic neurons is thought to be fundamental to the memory loss of Alzheimer's disease. The participation of NGF as a trophic factor for cholinergic neurons of the basal forebrain and the selective degeneration of ascending cholinergic projections from the basal forebrain has led to the hypothesis that reductions in NGF may contribute to the pathogenesis of Alzheimer's disease. However, the possibility that Alzheimer's disease might be associated with immune mechanisms that modify the interaction of nerve growth factor with its receptor has not yet been entertained.

Using the methods of the present invention, an antibody that immunoprecipitates [$^{125}$I]-2.5S-NGF has been detected in the serum (Table 16). The antibody binds to NGF in the ELISA (Table 17) and has been isolated using affinity chromatography (Table 18). Antibody to 7S NGF has been detected in patients wtih Alzheimer disease and age-matched normals and a patient with breast cancer. However, only the patients with Alzheimer's disease and the patient with breast cancer manifest binding to 2.5S NGF, the biologically active NGF, suggesting that activity against 7S NGF in the controls may be against biologically insignificant epitopes.

TABLE 16

Serum Immunoprecipitation of $^{125}$-I 2.5S Nerve Growth Factor

| Subject | CPM | % |
|---|---|---|
| Control | 7,528 | |
| 1. AD | 379 | 5 |
| 2. | 825 | 11 |

TABLE 16-continued

Serum Immunoprecipitation of $^{125}$-I 2.5S Nerve Growth Factor

| Subject | CPM | % |
|---|---|---|
| 3. | 1,158 | 15 |
| 4. AD | 483 | 6 |
| 5. AD | 10 | 0 |
| 6. AD | 670 | 9 |
| 7. AD | 946 | 13 |
| 8. AD | 1,741 | 23 |
| 9. AD | 1,669 | 22 |
| 10. AD | 2,016 | 27 |
| 11. AD | 801 | 11 |
| 12. | 1,144 | 15 |
| 13. | 698 | 9 |
| 14. | 460 | 6 |
| 15. AD | 1,547 | 21 |
| 16. | 1,854 | 25 |
| 17. | 1,440 | 19 |
| 18. | 1,384 | 18 |
| 19. | 1,099 | 15 |
| 20. | 0 | 0 |

IgG concentrations were equilibrated to 1.0 mg/100 μl by radial immunodiffusion (Meloy Laboratories). The assay was perormed by incubating a 100 μl volume of serum with 100 μl of $^{125}$-I 2.5S NGF overnight. Free radiolabeled NGF was adsorbed to activated charcoal.

TABLE 17

Anti-Mouse Nerve Growth Factor and Anti-Somatostatin Activity in IgG

| Subject | Age | Sex | Anti-NGF 2.5S Activity | Anti-NGF 7S Activity | Anti-Somatostatin Activity |
|---|---|---|---|---|---|
| Blind Alzheimer's/Normal Controls: | | | | | |
| 1. AD | 79 | F | 0 | 0.424 | 0.508 |
| 2. | 43 | F | 0 | 0.113 | 0.225 |
| 3. | 66 | F | 0.039 | 0.237 | 0.497 |
| 4. AD | 63 | M | 0.047 | 0.035 | 0.196 |
| 5. AD | 73 | F | 0.022 | 0.062 | 0.423 |
| 6. AD | 45 | F | 0 | 0.087 | 0.712 |
| 7. AD | 57 | F | 0.013 | 0.052 | 0.236 |
| 8. AD | 45 | F | 0.002 | 0.084 | 0.208 |
| 9. AD | 72 | F | 0.020 | 0.251 | 0.626 |
| 10. AD | 60 | F | 0.020 | 0.384 | 0.373 |
| 11. AD | 42 | M | 0.174 | 0.524 | 0.505 |
| 12. | 75 | F | 0.142 | 0.111 | 0.173 |
| 13. | 73 | M | 0.027 | 0.474 | 0.779 |
| 14. | 43 | M | 0.030 | 0.292 | 0.312 |
| 15. AD | 62 | M | 0.151 | 1.184 | 0.357 |
| 16. | 62 | M | 0.064 | 0.101 | 0.192 |
| 17. | 70 | F | 0.068 | 0.129 | 0.148 |
| 18. | 66 | F | 0.036 | 1.261 | 0.770 |
| 19. | 63 | F | 0.039 | 0.725 | 0.387 |
| 20. | 60 | F | 0 | 0.376 | 0.273 |
| Major Depression with Proven Anti-Somatostatin IgG: | | | | | |
| 21. | 54 | F | ND | 0.134 | 1.482 |
| 22. | 60 | F | ND | 0.364 | 0.697 |
| Young Normal Volunteers | | | | | |
| 23. | 28 | F | 0.027 | 0.058 | 0.070 |
| 24. | | F | 0 | 0.036 | 0.022 |
| 25. | 35 | F | 0.002 | 0.027 | 0.022 |
| 26. | | F | 0 | 0.044 | 0.020 |
| 27. | 32 | F | 0.002 | 0.047 | 0.107 |
| 28. | 42 | F | 0.002 | 0.081 | 0.021 |

IgG was isolated by affinity chromatography on Protein A. All samples were equilibrated to an IgG concentration of 2.7 μg/100 μl and assayed against fresh antigen at a concentration of 1 μg/100 μl. Sample values reflect the means of triplicate $OD_{405}$ for reactivity with either mouse nerve growth factor or somatostatin minus the reactivities with human ACTH fragment 1-39. Background binding to ACTH uniformly did not exceed 0.037 ± .009. Background
binding to a fourth human neuropeptide, β-endorphin, remained less than 0.050.

TABLE 18

Affinity Chromatography Purified Anti-7S-Nerve Growth Factor IgG

| Subject | [IgG] | 2.5S NGF | 7S NGF | ACTH 1–39 | Somatostatin |
|---|---|---|---|---|---|
| 1. AD eluate | 700 | 0.023 ± .002 | 0.050 ± .006 | 0.038 ± .003 | 0.600 ± .066 |
| 2. Normal | | | | | |
| eluate | 1,800 | 0.064 ± .001 | 0.080 ± .004 | 0.065 ± .003 | 0.071 ± .003 |
| effluent | 1,800 | 0.081 ± .002 | 0.446 ± .047 | 0.088 ± .005 | 0.153 ± .006 |
| 6. AD | | | | | |
| eluate | 1,000 | 0.164 ± .001 | ND | 0.087 ± .003 | 0.255 ± .077 |
| effluent | 2,500 | 0.176 ± .030 | ND | 0.061 ± .036 | 1.014 ± .068 |
| 9. AD | | | | | |
| eluate | 700 | 0.512 ± .001 | ND | 0.137 ± .026 | 0.890 ± .034 |
| effluent | 1.400 | 0.031 ± .001 | ND | 0.031 ± 0 | 0.026 ± .001 |
| 10. AD | | | | | |
| eluate | 200 | 0.029 ± .003 | 1.180 ± .061 | 0.292 ± .181 | 1.187 ± .047 |
| effluent | 200 | 0.027 ± .003 | 1.436 ± .032 | 0.365 ± .033 | 1.350 ± .070 |
| 15. AD | | | | | |
| eluate | 410 | 0.353 ± .082 | 1.427 ± .103 | 0.087 ± .034 | 0.193 ± .048 |
| effluent | 2,343 | 0.087 ± .008 | 1.296 ± .041 | 0.133 ± .080 | 1.201 ± .152 |
| 18. Breast Ca | | | | | |

TABLE 18-continued

Affinity Chromatography Purified Anti-7S-Nerve Growth Factor IgG

| Subject | [IgG] | 2.5S NGF | 7S NGF | ACTH 1-39 | Somatostatin |
|---|---|---|---|---|---|
| eluate | 1,800 | 0.319 ± .077 | 1.371 ± .121 | 0.113 ± .004 | 0.242 ± .007 |
| effluent | 1,800 | 0.042 ± .005 | 0.085 ± .007 | 0.070 ± .006 | 0.073 ± .004 |
| 20. Normal | | | | | |
| eluate | 1,800 | 0.067 ± .003 | 0.079 ± .002 | 0.065 1 .003 | 0.071 ± .003 |
| effluent | 1,800 | 0.070 1 .004 | 0.107 1 .011 | 0.060 1 .002 | 0.058 1 .004 |
| 21. Depressed | | | | | |
| eluate | 2,700 | 0.183 ± .052 | 1.408 ± .091 | 0.112 ± .001 | 0.153 ± .053 |
| effluent | 2,700 | 0.087 ± .013 | 0.184 ± .016 | 0.079 ± .009 | 0.062 ± .012 |

As shown in Table 19, of the samples tested thus far, only the anti-7S NGF antibody isolated from patients with Alzheimer's disease has activity against 2.5 S NGF.

TABLE 19

Anti-7S- Nerve Growth Factor IgG Immunoprecipites $^{125}$-I 2.5S NGF

| | | |
|---|---|---|
| 1. AD | 700 ng | 16% |
| 6. AD | 1,000 | 17% |
| 9. AD | 700 | 21% |
| 15. AD | 300 | 14% |
| 21. Depression | 300 | 4% |
| Normal | 300 | 5% |

In summary, the data presented herein clearly demonstrate that the detection of human antibodies to neuropeptides require very different conditions than those required to detect experimentally induced animal antiserums to neuropeptides. Rabbit antiserums could be detected using the usual recommended ELISA conditions. Critical factors that set this invention apart from usual ELISA methods are:

a. The utilization of a 24 to 48 hour incubation period at about 0°–4° C. in which human peptide solutions after centrifugation are allowed to coat the plate. This allows for complete coating while preventing the deterioration of temperature sensitive epitopes and peptides that might otherwise occur at higher temperatures. Rabbit antisera could be detected with the usual recommended 3 hour at room temperature to overnight (16 hour) coating period.

b. A minimum of 5 wash cycles at each step and omission of a blocking step help to eliminate the problem of nonspecific background binding. Some neuropeptides are "sticky," and, serum or IgG may stick to the peptide rather than bind to the peptide. Blocking proteins, such as bovine serum albumin, are greater than 20 times larger than neuropeptides in molecular weight, may stick to the neuropeptide and shield the neuropeptide from recognition by the human antibody. Additionally, human serum or IgG may stick to the blocking protein or potentially bind to trace amounts of serum neuropeptide in bovine serum albumin elevating the nonspecific background binding and confusing any interpretation of results. The recommended 3 washes for usual ELISA methods results in higher nonspecific background binding and wide variance in optical density readings for specific binding of human antibody to the neuropeptide, although rabbit antisera data was unaffected by 3 washes.

c. The employment of physiological temperatures at about 37° C. in humidified air with 5–7% $Co_2$ at subsequent steps in the ELISA to improve the binding of human serum or IgG to the neuropeptide, as well as, improve the detection of said binding using a second antibody conjugate. Commercial anti-human antibody conjugates mush be used in dilutions of 1:200 to 1:500 for optimum detection of human anti-neuropeptide antibodies; these dilutions are more concentrated than the usual >1:1000 dilutions used in usual ELISA methods. Rabbit antisera could be run at room temperature for each step with second antibody conjugate dilutions of 1:1000.

d. The employment of a direct ELISA rather than an indirect sandwich ELISA. The indirect ELISA proved suitable for animal antiserums but were complicated by nonspecific binding and considerable intra-test and inter-vest variability when using human sera or IgG.

The pathophysiology of neuropsychiatric disorders has remained obscure largely as a result of the inability to directly observe physiological dysfunction within the CNS. The lack of clinicopathologic correlation between patients' symptoms in life and the absence of neuropathology at autopsy examination has severly limited direct anatomical an d pathophysiological insight into these disorders. As a result, after several hundred years the diagnosis of psychiatric disorders continues to rest upon the classification of phenomenological observations. Consequently, medical science has been obligated to reason backwards from the observations of the effects of neuropharmacological agents on the in vitro pharmacology and physiology of neurons, their effects on indirect neuroendocrine measures when infused into humans, and their effects on the behavior of laboratory animals. The present ELISA for antibodies to brain peptides for the first time provides a window to directly observe the influence of the immune system on central nervous system functioning in humans. This methodology affords an additional vantage point in the attempt to elucidate the mechanisms and etiologies of psychiatric disorders that heretofore did not exist. The ELISA of the present invention, additionally allows the examination of cerebrospinal fluid for the presence of these antibodies.

Of course, an established correlation between the level of antibodies to brain peptides and psychobiological conditions may provide a marker of psychiatric disease. It is postulated that elevated levels of antibody to neuropeptides will be detected only in those medical disorders which are associated with psychiatric impairment and alterations in brain peptides, e.g., the ectopic production of B-endorphin, somastostatin, nerve growth factor and the like by a neoplasm, neurological disorders with neuroimmunological alterations such as multiple sclerosis, or viral or parasitic infections with prominent CNS infiltration, e.g. AIDS. IN effect, a simple blood test in accordance with the ELISA of the present invention makes it possible to corroborate or establish a psychiatric diagnosis of those conditions which are related to an alteration in the normal level of neuropeptides or their receptors or interaction thereof and it will definitively detect the clinical presence of antibodies to such neuropeptides or their receptors that may function other medical disorders.

It is understood that the examples and embodiments described herein are for illustrative purposes only and that various modifications or changes in light thereof will be suggested to persons skilled in the art and are to be included within the spirit and purview of this application and the scope of the appended claims.

I claim:

1. A method for detecting in a sample of human body fluid the presence of specific antibodies against brain peptides or brain drugs comprising the steps of:
   (a) coating a multiwell plate with a solution of neuropeptide or brain drug to be detected, by incubating the plate for more than 24 hours with said solution at about 0° to 4° C. without a blocking step;
   (b) then allowing a sample of immunoglobulin containing human body fluid in which the presence of antibody to th e neuropeptide or brain drug is to be detected, to react with the coated plate in humidified air containing about 5-7% $CO_2$ for about 1.5 to 3 hours at 37° C.;
   (c) then washing the plate with a buffered detergent more than 5 times to remove unbound material from the plate;
   (d) then allowing anti-human antibody conjugated with a marker entity to react for about 1.5 to 3 hours in humidified air containing about 5-7% $CO_2$ at about 37° C. with the washed plate of step (c) to allow binding of the conjugated-antibody with the human antibody bound to the neuropeptide or brain drug;
   (e) then removing the unreacted material from the plate by washing more than 5 times as in step (c);
   (f) then determining the presence of the marker by enzymatic, spectrophotometric, fluorscentphotometric or radioisotopic assay and comparing with a control sample treated identically as in step (a) thru (e), a reading above the control being indicative of the presence of antibody against the neuropeptide or the brain drug.

2. A method for diagnosing a psychobiological disorder in a human comprising detecting the presence of a certain level of antibodies to a specific neuropeptide in a sample of human body fluid by the method of claim 1 and establishing a correlation between the level of said antibody and a known standard level of said antibody for a psychobiological disorder.

* * * * *